United States Patent [19]

Meehan

[11] Patent Number: 4,528,657
[45] Date of Patent: Jul. 9, 1985

[54] FLUID SAMPLE CELL FOR X-RAY ANALYSIS

[75] Inventor: Patrick J. Meehan, Penfield, N.Y.

[73] Assignee: E. I. Du Pont de Nemours and Company, Wilmington, Del.

[21] Appl. No.: 464,422

[22] Filed: Feb. 7, 1983

[51] Int. Cl.³ .................... H01J 37/20; G01N 23/22
[52] U.S. Cl. ........................................ 378/47; 378/79
[58] Field of Search ............................. 378/47, 79, 80

[56] References Cited

U.S. PATENT DOCUMENTS

| 2,819,402 | 1/1958 | Watson et al. | |
| 3,218,459 | 11/1965 | Bens | 378/47 |
| 3,354,308 | 11/1967 | Engel | 378/47 |
| 3,602,711 | 8/1971 | Arora et al. | |
| 3,751,661 | 8/1973 | Packer | 378/47 |
| 3,999,867 | 12/1976 | Stabell | |

OTHER PUBLICATIONS

E. P. Bertin, *Solution Techniques in X-Ray Spectrometric Analysis*, Norelco Reporter V12, #1, pp. 15-26 (1965).
M. C. Lambert, *Some Practical Aspects of X-Ray Spectrography*, Norelco Reporter V6, pp. 37-51 (1959).
E. P. Bertin, *Recent Advances in Quantitative X-Ray Spectrometric Analysis by Solution Techniques*, Advan X-Ray Anal. 11, pp. 1-22 (1968).
W. J. Campbell, M. Leon, J. W. Thatcher, *Solution Techniques in Fluorescent X-Ray Spectrography*, U.S. Bureau of Mines Report #5497, Dept. of the Interior (1959).
W. J. Campbell, *Apparatus for Continuous Fluorescent X-Ray Spectrographic Analysis of Solutions*, Applied Spectroscopy, vol. 14, #1, pp. 26-27 (1960).
E. L. Gunn, *X-Ray Spectrometric Anal. of Liquids and Solutions*, Amer. Soc. Test Mater. Spec. Tech. Pub. V349, p. 7085 (1964).

Primary Examiner—Craig E. Church

[57] ABSTRACT

A cell for introducing fluid to be examined into a radiation path. The cell is constructed of metallic back and face plates, the back plate has a cavity for the fluid while the face plate presents a cavity with a thin layer of metal defining an aperture for X-rays.

3 Claims, 7 Drawing Figures

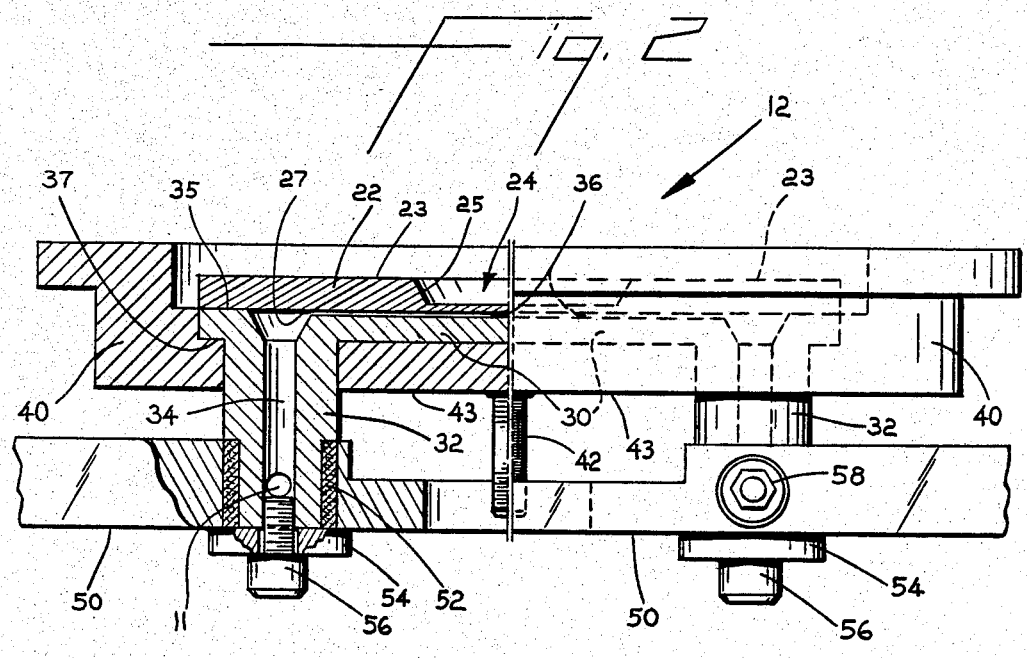
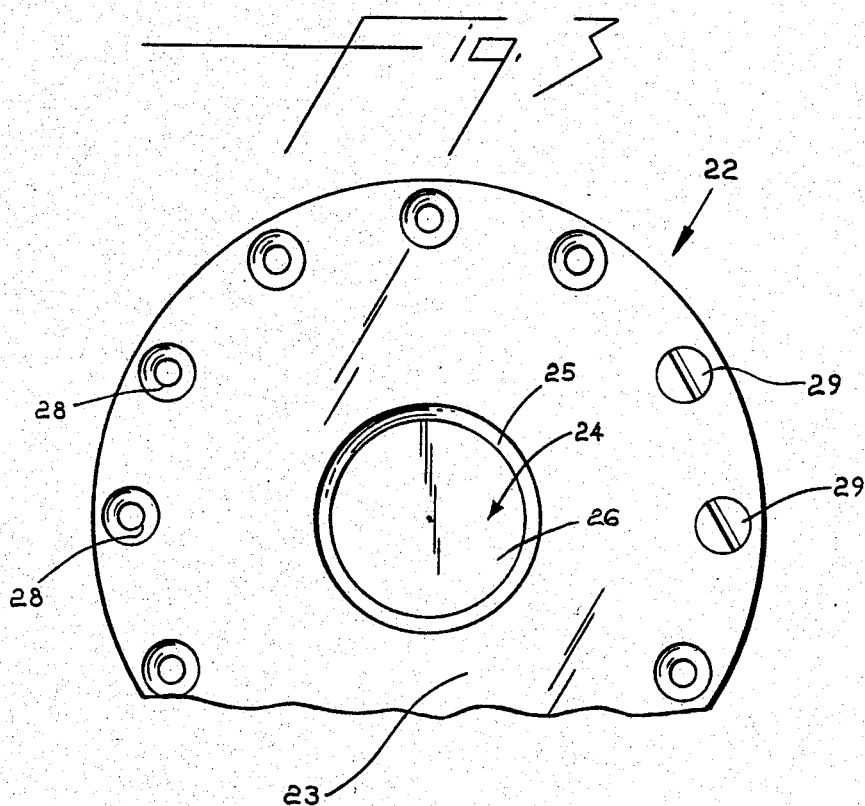

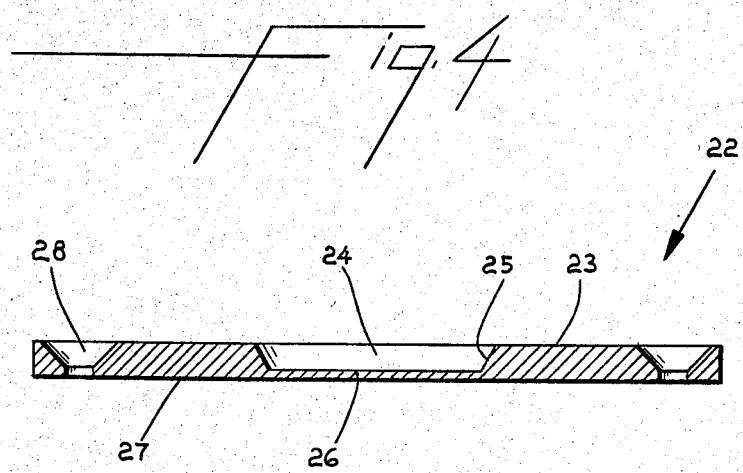
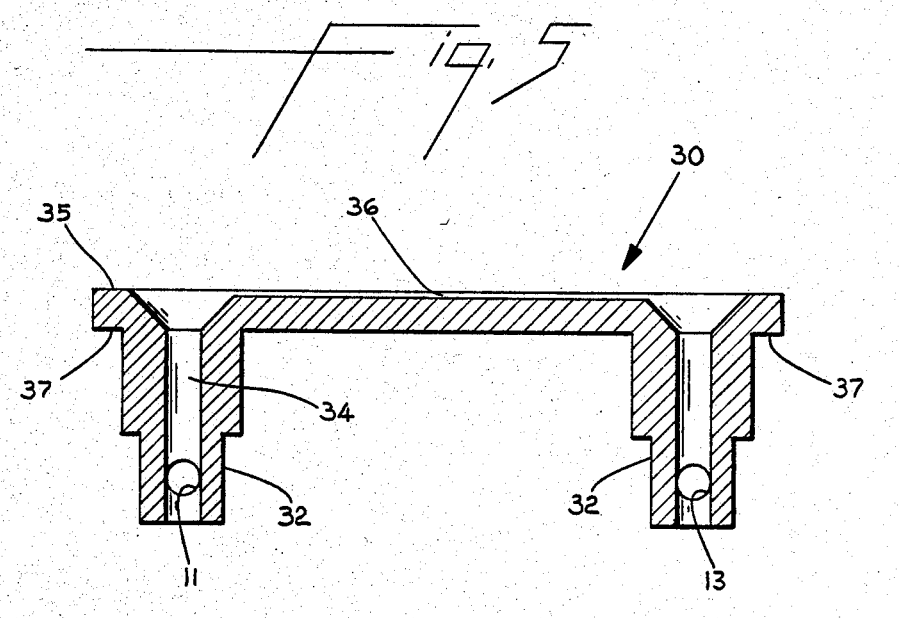

FLUID SAMPLE CELL FOR X-RAY ANALYSIS

BACKGROUND OF THE INVENTION

This invention relates to X-ray fluorescence spectrometry, and more particularly, it relates to a cell into which a liquid sample is introduced for examination.

X-ray secondary emission or fluorescence spectrometry is recognized as a versatile instrumental technique for chemical analysis. The analyses are rapid and convenient, especially when the samples are analyzed in their original form. In such a technique, the sample is irradiated by the primary X-ray beam and excites secondary emissions of wavelengths characteristic of elements in the sample and of intensities related to their concentrations.

It is known in the art that liquid samples can be loaded in or flow continuously through a cell depending on the particulars of a given analysis. The problem experienced with known flow cells is that the face plate through which a sample is irradiated is either so thick as to absorb energy or so thin as to bend due to the pressure drop across the cell. In the latter instance, the volume of the cell is increased temporarily, resulting in a spurious X-ray count.

The presentation of a thin flowing analyte layer provides the advantages embodied in known designs such as turbulent flow which prevents separation of suspensions and reduces radiation induced sample reactions by limiting exposure duration. The thin analyte layer also provides improved X-ray signal to concentration linearity by reducing matrix absorption and enhancement effects.

SUMMARY OF THE INVENTION

A cell for X-ray analysis of a liquid sample has inflexible metallic back and face plates sandwiched in bearing engagement to each other. The back plate has an inner surface with a shallow cavity for a sample. The face plate has a planar inner surface and an outer surface provided with a shallow cavity presenting a thin layer of metal defining an aperture for X-rays. Preferably the face plate is constructed of titanium which is selected for its properties of chemical corrosion resistance to emulsion, transparency to X-rays, resistance to X-ray radiation damage and physical rigidity. The back plate is made from stainless steel. Inlet and outlet passages connected with the shallow cavity in the back plate are provided so that the cell of the invention may be used with a continuously flowing process sample or used for individual and separate analysis of discrete samples.

BRIEF DESCRIPTION OF THE DRAWINGS

FIG. 2 is a side elevation view of the cell of the present invention, parts having been broken away and shown in section to reveal details of construction;

FIGS. 3 and 4 are top and transverse sectional views of the face plate in the assembly of FIG. 2;

FIGS. 5 and 6 are sectional and bottom plan views of the back plate in the assembly of FIG. 2;

DETAILED DESCRIPTION OF THE PREFERRED EMBODIMENT

Figure 1:
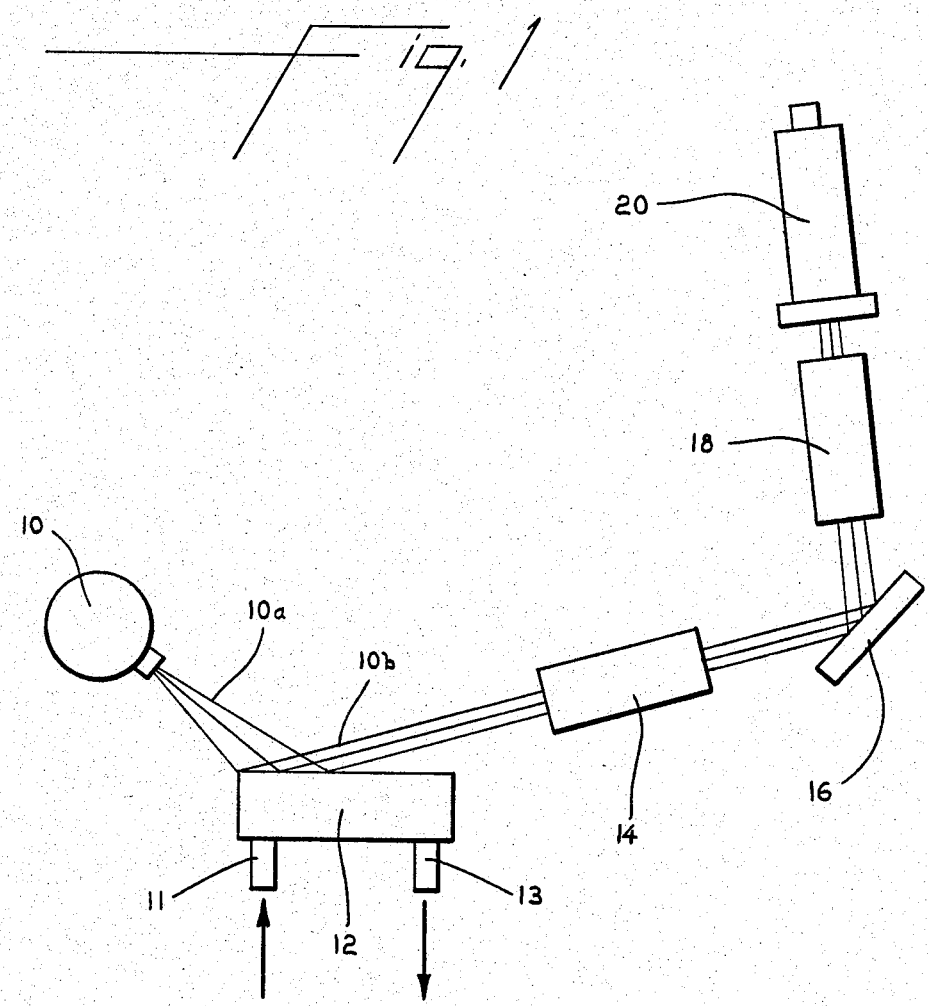
FIG. 1 is a schematic illustration of essential components for the excitation and measurement of X-ray fluorescence spectra.
Figure 6:
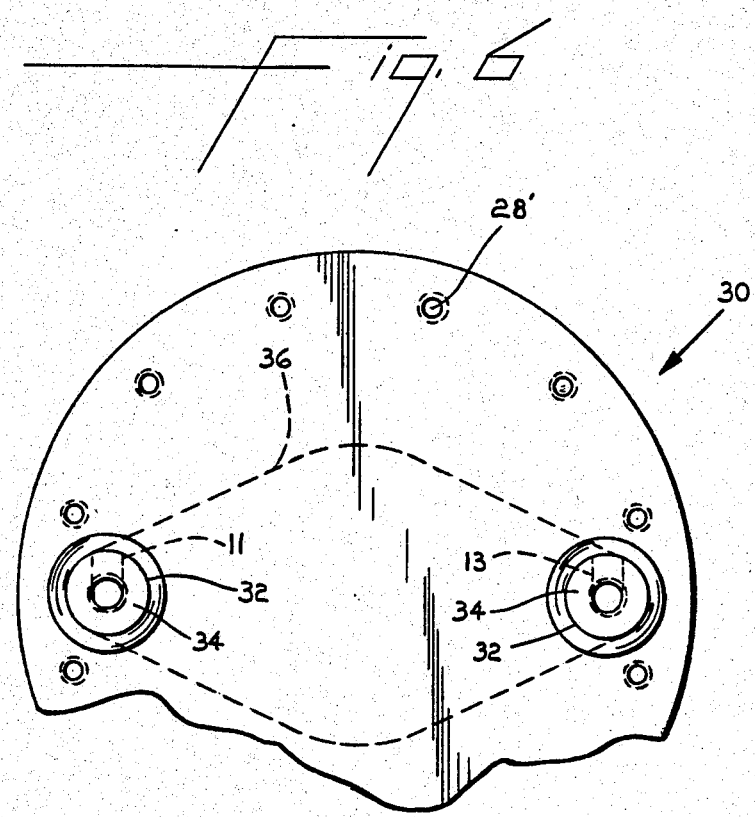
Figure 7:
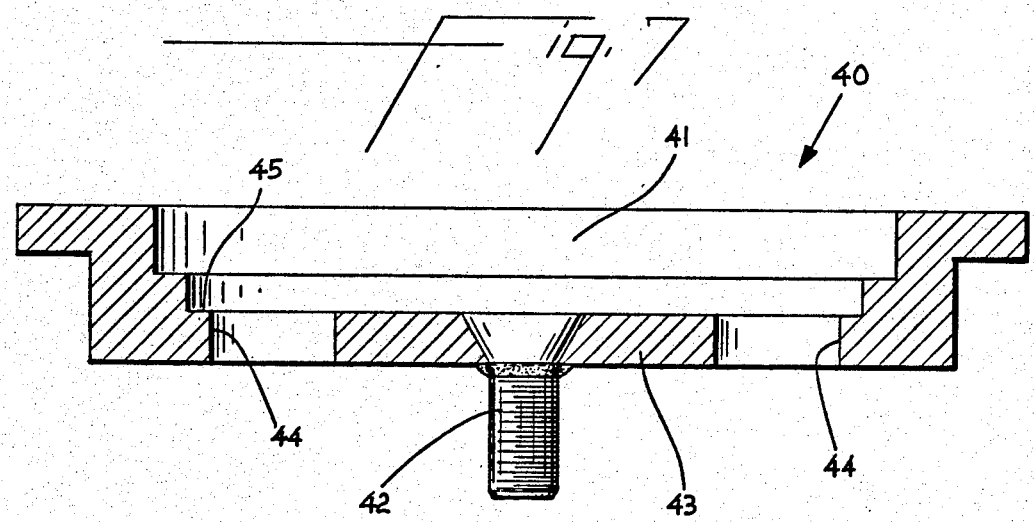
FIG. 7 is a sectional view of the mounting cup of FIG. 2.

Referring to FIG. 1, the embodiment chosen for purposes of illustrating the essential components for the excitation and measurement of X-ray fluorescence spectra generally includes an X-ray tube 10, directed toward a sample cell 12, a primary collimator 14, an analyzing crystal 16, a secondary collimator 18 and a detector 20. The sample cell includes an inlet passage 11 and outlet passage 13 which may be connected to a continuously flowing process sample as in a process stream analysis. However, these passages may also be used to introduce discrete samples into the cell for individual and separate analysis.

In operation, the primary X-ray beam 10a irradiates the sample in cell 12 exciting secondary emissions 10b of wavelengths characteristic of the elements in the sample and of intensities related to their concentration. The spectrometer (primary collimator 14, analyzing crystal 16, secondary collimator 18 and detector 20) measures the wavelengths and intensities of the spectral lines 10b emitted by the samples.

Referring now to FIGS. 2–7, the sample cell 12 consists generally of a face plate 22, a back plate 30, a retaining cup 40 and a base 50 serving as a connector between the sample supply and the back plate 30. The two principal parts of the cell are the face plate 22 and the back plate 30 with their inner surfaces sandwiched in bearing engagement, i.e., the inner surface 35 of the back plate and planar inner surface 27 of face plate. Both plates are cylindrical in shape and formed from metal. Screws 29 passing through holes 28 and threaded into holes 28' in back plate 30 hold the plates together in bearing and sealing engagement. The outer surface 23 of the face plate 20 is provided with a circular central cavity 24 defined by a tapered sidewall 25 and a thin bottom layer 26. The cavity 24 is an aperture for X-rays being emitted from tube 10. A shallow cavity 36 is formed in the inner surface 35 of back plate 30 for the sample which enters through entry port 11 and flows through passage 34 in leg 32 of the back plate. Thus the cavity 36, the entry port 11, passage 34 and exit port 13 are in communication with each other, and in continuous operation, the fluid sample would flow into port 11 and out from port 13.

A mounting cup 40 has a stepped recess 41 to receive the sandwiched plates 22 and 30 with shoulder 37 of back plate 30 resting on shoulder 45 of recess 41. The cup 40 has a mounting bolt 42 welded to its base 43 for mounting the assembled cell in an X-ray analyzing instrument. The connector base 50 is held and sealed to the legs 32 by means of bolts 56 threaded into the legs, washers 54 and gaskets 52 providing a seal between the legs 32, and the base 50. A hollow bolt 58 is threaded through base 50 into ports 11 and 13 leading to passages 34 in legs 32 of back plate 30. A sample is fed from its source to the cell via the hollow bolt 58.

A useful embodiment of the sample cell 12 of this invention employed a back plate 30 of Type 316 stainless steel and a face plate 22 of titanium. The face and back plates were about 2 inches (5.08 cm) in diameter and about 0.100 inch (0.254 cm) thick. The depth of the cavity 36 in the back plate was about 0.020 inch (0.51 cm). The centrally located aperture 24 in the face plate was approximately 0.500 inch (1.27 cm) in diameter and milled to a depth to leave a thickness of about 0.007 inch (0.018 cm).

In operation, the thickness of the analyte layer is governed by the depth of cavity 36 and must be sufficient for an adequate X-ray signal. However, to insure that a uniform sample flow is seen by the X-rays, the aperture 24 is provided in the face plate 22. The face plate at the aperture must be as thin as possible to allow maximum X-ray energy to pass through and be reflected, but rigid enough to resist deformation due to the pressure drop across the cell. If the plate isn't thick enough to avoid bending, temporary variations in volume of the cell cavity will occur and destroy the linearity in the relationship between X-ray count and concentration of the substance being analyzed.

The cell shown in FIG. 2 achieves a balance between these effects and provides such linearity. The aperture 24 is milled into the surface of the face plate 22 to achieve thinness and least resistance to passage of X-rays. Binding is avoided by leaving a thicker border connected to the thin section 26 of the aperture by a tapered length 25, and of course by selecting titanium as the material for the face plate.

I claim:

1. A cell for the X-ray analysis of a liquid sample, said cell comprising: inflexible metallic back and face plates sandwiched in bearing engagement, said back plate having an inner surface provided with a shallow cavity for a sample, said face plate having a planar inner surface and an outer surface provided with a cavity presenting a thin layer of metal defining an aperture for X-rays.

2. The cell as defined in claim 1, including inlet and outlet passages in communication with said shallow cavity.

3. The cell as defined in claim 1, said face plate consisting essentially of titanium, said back plate comprising stainless steel.

* * * * *